United States Patent [19]

Van Le et al.

[11] Patent Number: 5,250,704
[45] Date of Patent: Oct. 5, 1993

[54] PROCESS FOR THE MANUFACTURE OF (S)-3-AMINO-1-SUBSTITUTED-PYRROLIDINES

[75] Inventors: Tung Van Le, Jenison; F. Gregory Spence; James N. Wemple, both of Holland, all of Mich.

[73] Assignee: Warner-Lambert Company, Morris Plains, N.J.

[21] Appl. No.: 943,343

[22] Filed: Sep. 10, 1992

Related U.S. Application Data

[62] Division of Ser. No. 874,657, Apr. 27, 1992, Pat. No. 5,177,217.

[51] Int. Cl.$^5$ .............. C07D 207/14; C07D 203/08; C07D 203/24
[52] U.S. Cl. .................... 548/557; 548/965; 548/968
[58] Field of Search .............. 548/965, 968, 557

[56] References Cited

PUBLICATIONS

CA 72(5) 21246m Reaction of N,N-Dichloroethanesulfonamide with 1-Olefins, Ohashi et al., p. 266, 1970.
CA 88(23):170040x Some Reactions of Diazomethane with Polyfluoroazaolefins, Coe et al., p. 583, 1978.

*Primary Examiner*—Mary C. Lee
*Assistant Examiner*—Joseph K. McKane
*Attorney, Agent, or Firm*—Ronald A. Daignault

[57] ABSTRACT

A novel process for preparing a stereospecific (S)-3-amino-1-substituted pyrrolidine used as a key intermediate in preparing quinolone and naphthyridone antibacterial agents where the 7-position is occupied with a sterospecific 3-aminopyrrolidine side chain is described starting from inexpensive L-aspartic acid. L-aspartic acid is converted to the desired (S)-3-aminopyrrolidine via a novel, high yield transformation of a substituted aziridine.

3 Claims, No Drawings

PROCESS FOR THE MANUFACTURE OF (S)-3-AMINO-1-SUBSTITUTED-PYRROLIDINES

This is a divisional of U.S. application Ser. No. 874,657 filed Apr. 27, 1992, U.S. Pat. No. 5,177,217.

BACKGROUND OF THE INVENTION (S)-3-Amino-1-benzylpyrrolidine and (S)-3-[(S)-2-{tert-butoxycarbonylamino}-propionylamino] pyrrolidine are key intermediates required for the synthesis of several quinolone antibacterial agents disclosed, for example, in U.S. Pat. Nos. 4,851,418 and 4,916,141. Known processes for the synthesis of optically active 3-amino-1-substituted-pyrrolidines include the conversion of 1-benzyl-3-pyrroline to (S)-3-amino-1-benzylpyrrolidine in four steps in 60% overall yield with an enantiomeric excess of 84% (H. C. Brown, J. V. N. Vara Prasad, A. K. Gupta, *J. Org. Chem.*, 51, 4296 (1986); T. Rosen et al, *J. Med. Chem.*, 31, 1586 (1988); D. T. W. Chu, T. J. Rosen, European Patent Application EP 331,960). This process uses the relatively expensive hydroboration reagent, diisopinocampheylborane. In a second process trans-4-hydroxy-L-proline is converted into (S)-3-amino-1-(benzyloxycarbonyl)-pyrrolidine in five steps in 77% overall yield with an enantiomeric excess greater than 99%, U.S. Pat. No. 4,851,418; however, the trans-4-hydroxy-L-proline starting material is expensive. Racemic 3-amino-1-benzylpyrrolidine has been resolved in low yield by fractional crystallization of the salt with L-tartaric acid (Tokyo Ksei Kogyo, Japanese Patent J02218-664A (1989). Chiral butane derivatives with leaving groups (chloro or methanesulfonyloxy) at positions 1, 2, and 4 were treated with primary amines to give chiral 3-(substituted amino)-1-substituted pyrrolidines (Tokyo Kasei Kogyo, Japanese Patent J91020-391-B (1987); European Patent Publication 443498)). Finally the relatively inexpensive L-aspartic acid was converted to (S)-3-amino-1-phenylpyrrolidine via 3-[N-(tert-butoxycarbonyl)amino]-1-phenylpyrrolidine-2,5-dione, although in low overall yield (D. T. Witiak, et al, *J. Med. Chem.*, 14, 24 (1971).

Due to its low cost, L-aspartic acid appears to be the most attractive starting material for the preparation of (S)-3-amino-1-substituted-pyrrolidines. The literature method from L-aspartate (D. T. Witiak, loc. cit.) involves treatment of N-boc-L-aspartate with acetic anhydride to give (S)-3-(tert-butoxycarbonylamino)succinic anhydride followed by addition of a primary amine and ring closure with heat to give the succinimide, (S)-3-(tert-butoxycarbonylamino)-1-substituted pyrrolidine-2,5-dione. The latter is then reduced and deblocked to give the 1-substituted-3-aminopyrrolidine in low overall yield. From our experience with this method some racemization takes place when the blocking group is p-toluenesulfonyl(tosyl) and the primary amine is benzylamine.

We have now found an alternate, high yield method for converting L-aspartic acid to (S)-3-amino-1-substituted pyrrolidines which involves the synthesis of (S)-2-(2'methanesulfonyloxyethyl)-1-(p-toluenesulfonyl)aziridine and its conversion to (S)-1-benzyl-3-(p-toluenesulfonylamino)pyrrolidine as the key steps. The method may be extended to the synthesis of other optically active 3-amino pyrrolidines with different substituents (R') at the 1 position.

SUMMARY OF THE INVENTION

Accordingly, the present invention is a commercially viable process for the preparation of (S)-3-amino-1-substituted pyrrolidines of the formula

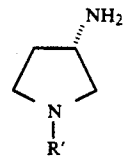

wherein R' is benzyl, benzyl substituted by lower alkyl or lower alkoxy, or benzhydryl, which comprises
(1) blocking the amino group of L-aspartic acid with an alkyl or arylsulfonyl blocking group;
(2) reducing the N-blocked-L-aspartic acid, or di-lower alkyl-ester thereof with a hydride reducing agent;
(3) reacting the N-blocked-1,4-butanediol with about two equivalents of a thionyl halide or an alkyl- or arylsulfonyloxy halide in the presence of about three equivalents of a base to form a compound of the formula

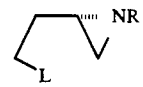

wherein L is halo or alkyl- or arylsulfonyloxy and R is an alkyl or arylsulfonyl group;
(4) reacting the product of step (3) with R'—NH$_2$ in the presence of a tertiary amine to form a 1-R'-3-(blocked amino)-pyrrolidine in which R' is as defined above, and
(5) removing the blocking group by hydrolysis or reduction to afford the desired product.

DETAILED DESCRIPTION

In the preparation of (S)-3-amino-1-substituted pyrrolidines of the formula I, the following terms are herein defined.

Lower alkyl refers to a straight or branched chain of a hydrocarbon radical having from one to six carbon atoms, such as, for example, methyl, ethyl, propyl, (methyl)ethyl, butyl, 1,1-(dimethyl)ethyl, and the like.

Lower alkoxy refers to a hydroxyl radical whose hydrogen atom has been replaced by lower alkyl as defined above.

An alkylsulfonyl halide or alkanesulfonyl halide is a sulfonyl halide containing a lower alkyl substituent defined above.

An arylsulfonyl halide is a sulfonyl halide containing aryl defined as phenyl or phenyl substituted by one to three substituents selected from lower alkyl, lower alkoxy, halo, trifluoromethyl and nitro, and combinations thereof.

Halide or halo means a halogen atom such as fluorine, chlorine, bromine or iodine.

A base is an organic or inorganic base. An organic base is an amine, preferably a tertiaryamine, such as, for example, triethylamine, pyridine, quinuclidine and the like. An inorganic base is an alkali or alkaline earth metal hydroxide or carbonate, such as, for example, sodium or potassium hydroxide or carbonate, and the like.

An amino blocking or protecting group is preferably a group derived from a sulfonic acid or derivative thereof capable of replacing an available hydrogen atom on an amino group and such group being capable of being easily removed by hydrolysis or reduction. Such groups are for example, alkyl or arylsulfonyl, such as methylsulfonyl, benzenesulfonyl, p-toluenesulfonyl and the like.

Other reagents and preferred embodiments are described in the process description.

The present invention is illustrated generally in the following Scheme I.

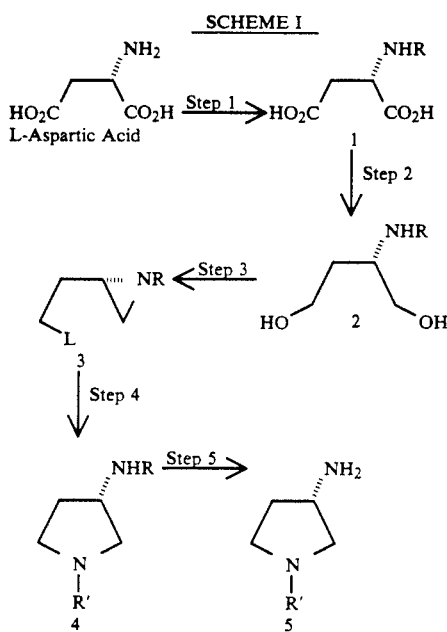

REACTION I involves the conversion of L-aspartic acid to a nitrogen blocked derivative of the amino acid in which the blocking group (R) may be p-toluenesulfonyl or some other arylsulfonyl derivative such as p-bromobenzene-sulfonyl, or it may be an alkanesulfonyl group such as methanesulfonyl. These compounds are available in high yield using standard literature methods. For example, N-tosyl-L-aspartate can be prepared according to the method of K. Freudenberg and A. Noe (Chem. Ber., 58, 2399 (1925)) or by the method of E. W. McChesney and W. K. Swann, Jr. (J. Am. Chem. Soc., 58, 1116 (1937)).

REACTION II involves the reduction of the N-blocked-L-aspartic acid derivative to the corresponding optically active 2-(blocked amino)-1,4-butanediol—either by direct reduction of the two carboxylic acid functions to two alcohol groups or by conversion to the corresponding diester followed by reduction of the two ester functions to two alcohol groups. Various hydride reducing reagents could be used to reduce the carboxylic acid functions in the L-aspartic acid derivatives such as borane ($B_2H_6$) or lithium aluminum hydride ($LiAlH_4$) or a combination of sodium borohydride ($NaBH_4$) and iodine ($I_2$). Sodium borohydride ($NaBH_4$) in the presence of LiCl, LiBr, $CaCl_2$, $MgCl_2$, $ZnCl_2$, or Lewis acid catalysts and also $LiAlH_4$ and vitride [$NaAlH_2(OCH_2CH_2OCH_3)_2$] would be effective in reducing the ester functions in the aspartic acid diester derivatives. Suitable solvents for these reduction reactions are aprotic solvents such as toluene, tetrahydrofuran, 1,2-dimethoxyethane or a related ether solvent. For the borohydride reductions, alcohol solvents such as methanol or ethanol are also suitable.

REACTION III involves the conversion of the optically active 2-(blocked amino)-1,4-butanediol to an optically active derivative of 2-(2'hydroxyethyl)-1-(blocked)aziridine in which the alcohol function is replaced with a leaving group (L) such as chloro or an alkanesulfonyloxy group such as the methanesulfonyl group or a arylsulfonyloxy group such as p-toluenesulfonyloxy. The aziridine derivatives containing a sulfonate ester leaving group can be prepared by treatment of the 2-(blocked amino)-1,4-butanediol with approximately two equivalents of an alkanesulfonyl chloride or an arylsulfonyl chloride and also approximately three equivalents of a base such as a tertiary amine base (e.g. triethylamine) or a carbonate base such as potassium carbonate in an aprotic solvent such as methylene chloride, tetrahydrofuran or toluene at −10° to 35° C. for 30 to 240 minutes. The aziridine derivatives containing a chloro leaving group can be prepared by treating the 2-(blocked amino)-1,4-butanediol with thionyl chloride in the presence of a suitable base such as triethylamine or pyridine in an aprotic solvent such as methylene chloride, tetrahydrofuran or toluene.

REACTION IV involves the conversion of the optically active derivative of 2-(2'hydroxyethyl)-1-(blocked)aziridine in which the alcohol group has been replaced with a leaving group into a 1-substituted-3-(blocked amino)-pyrrolidine by treatment of the aziridine with a primary amine such as benzyl amine or p-methoxybenzyl amine in the presence of a suitable base such as a tertiary amine (e.g. triethylamine) or a carbonate base (e.g. potassium carbonate) in an aprotic solvent such as DMSO, DMF, $CH_3CN$, toluene or THF at 10° to 110° C. for a 1 to 18-hour period. Excess primary amine may be separated from the product by treating a solution of the product mixture with carbon dioxide followed by extraction of the carbamic acid derivative of the primary amine into dilute aqueous sodium hydroxide solution. Alternatively, a solution of the product mixture may be treated with methyl formate to form the formamide derivative of the primary amine. This formamide may be extracted from the desired Step 4 pyrrolidine by extraction of the latter into aqueous acid. A third approach for separating the primary amine is to treat the product mixture with phthalic anhydride followed by removal of the resulting benzylamine adduct, a phthalic acid mono amide, by extraction into aqueous base.

REACTION V involves the removal of the blocking group from the 3-amino function by reduction of a sulfonamide blocking group. The 1-substituted-3-(blocked amino)pyrrolidine may be treated with hydrogen bromide in a suitable solvent such as water or acetic acid in the presence of a suitable bromine scavenging agent such as phenol, phosphorous, sulfur dioxide, or sodium hydrogen sulfite at 50° to 130° C. for periods of 1 to 10 hours to afford after workup the desired 3-amino-1-substituted pyrrolidine. Alternatively, the sulfonamide group may be removed by metal reduction with reagents such as sodium amalgam, potassium with a crown ether catalyst or sodium-naphthalene.

The (S)-3-amino-1-R'-pyrrolidine, 5, may be utilized to make antibacterial agents as in U.S. Pat. No. 4,916,141. First the amino group is blocked with a suitable carbamate protecting group, for example, tertiarybutoxycarboxyl or benzyloxycarbonyl, then the R' group is removed reductively with hydrogen and catalyst. The resulting (S)-3-protected aminopyrrolidine is reacted with the desired 7-halo-quinolone or 7-halo-naphthyridone to form the desired quinolone or naphthyridone. Alternate use of the (S)-3-amino-1-R'-pyrrolidine, 5, is further reacting pyrrolidine 5, as illustrated in Example 2, to provide an intermediate with two asymmetric carbon atoms, and then reacting this intermediate with the appropriate 7-halo-quinolone or naphthyridone to prepare antibacterial agents as in U.S. Pat. No. 4,851,418.

As a specific example and an illustration of the preferred embodiment of the present invention the process may be carried out using p-toluenesulfonyl as the blocking group (R) on the amino function in L-aspartic acid, methanesulfonyloxy as the leaving group (L) in intermediate 3 and benzyl as the substituent (R') at the one position of the pyrrolidine in intermediates 4, and 5 as shown in Scheme II.

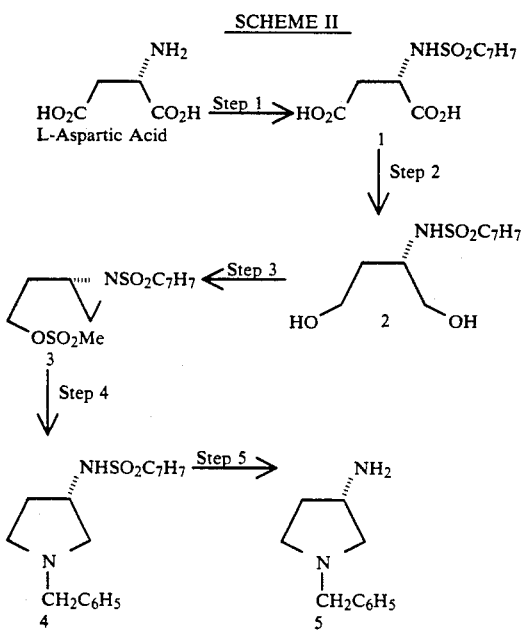

EXAMPLE 1

STEP 1: N-(p-Toluenesulfonyl)-L-aspartic acid, 1

L-Aspartic acid (239.4 g) was dissolved in 3N NaOH (1152 mL) and the solution cooled to 0° C. Tetrabutylammonium hydrogen sulfate (9 g) and tetrahydrofuran (240 mL) were added and the pH adjusted to 12.8 with 3N NaOH (160 mL). Using separate addition funnels a solution of p-toluenesulfonyl chloride (342 g) in tetrahydrofuran (675 mL) was added simultaneously with 3N NaOH (900 mL) over a 6 hour period while maintaining the temperature between 0° to 5° C. and the pH between 11.7 and 12.8. The reaction mixture is stirred overnight and the next day acidified to pH 2.6 with 400 mL 36% HCl. The mixture was extracted with ethyl acetate (2×1350 mL) and the combined ethyl acetate extracts concentrated to an oil. This was treated with toluene (2×1800 mL) and the resulting mixture concentrated under vacuum and the residue vacuum dried to give N-(p-toluenesulfonyl)-L-aspartic acid, 1, as an off-white solid (487.7 g, 94%) which was used directly in the next step without further purification.

STEP 2: (S)-2-(p-toluenesulfonylamino)-1,4-butanediol, 2

N-(p-Toluenesulfonyl)-L-aspartic acid, 1, (110 g) was dissolved in tetrahydrofuran (300 mL) and the solution cooled to −5° C. under a nitrogen atmosphere. A 1.0M solution of borane in tetrahydrofuran was added dropwise over 1 hour at 0 to −5° C. and the resulting solution stirred at 20° to 25° C. overnight. The solution was recooled to 0° C. and methanol (250 mL) was added dropwise over 30 minutes (caution! gas evolution). The solution was concentrated under vacuum to an oil which was redissolved in methanol (1L) and the solution heated at reflux 1 hour. This solution was concentrated under vacuum to give a solid which was redissolved in methanol (1L) and this solution heated at reflux for 2 hours. Finally the solution was concentrated to a solid which was dried under vacuum at 50° C. to give (S)-2-(p-toluenesulfonylamino)-1,4-butanediol, 2, as an off white solid (97 g, 98%) which was used directly in the next step without further purification. A portion was recrystallized from isopropyl alcohol and hexanes: mp 90°–92° C.

STEP 3: (S)-2-(2'-Methanesulfonyloxyethyl)-1-(p-toluenesulfonyl)aziridine (S)-2-(p-Toluenesulfonylamino)-1,4-butanediol, 2, (46 g) was dissolved in methylene chloride (450 mL) and triethylamine (60 g) was added. The resulting solution was cooled to −5° C. under a nitrogen atmosphere and a solution of methanesulfonyl chloride (42.0 g) in methylene chloride (110 mL) was added dropwise over 3 hours. The resulting mixture was stirred an additional 0.5 hour at 0° to −5° C. and water (150 mL) and methylene chloride (350 mL) were cautiously added. The layers were separated and the organic layer extracted with 0.1N HCl (100 mL) and demineralized water (100 mL) and then concentrated under vacuum to give (S)-2-(2'-methanesulfonyloxyethyl)-1-(p-toluenesulfonyl)aziridine, 3, as a light yellow solid (57.2 g) which was used directly in the next step without further purification. A portion was recrystallized from ethyl acetate and hexanes: mp 78°–80° C.

STEP 4: (S)-1-Benzyl-3-(p-toluenesulfonylamino)pyrrolidine, 4, and (S)-1-benzyl-3-(p-toluenesulfonylamino)pyrrolidine hydrochloride (S)-2-(2'-Methanesulfonyloxyethyl)-1-(p-toluenesulfonyl)aziridine, 3, (54.5 g) was dissolved in warm tetrahydrofuran (50 mL) and the solution added dropwise over 20 minutes to a solution of benzylamine (40 g) and triethylamine (40 g) in dimethyl sulfoxide (250 mL) at 75° to 85° C. The resulting solution was heated another 2.5 hours at 75° to 85° C. and then concentrated under vacuum to remove tetrahydrofuran and dimethyl sulfoxide. The residue was dissolved in toluene (300 mL) and cautiously treated with 10 g of dry ice followed by 1.0N NaOH (150 mL). The layers were separated and the toluene layer treated cautiously with more dry ice (3 g) followed by 20 mL 1.0N NaOH. This carbon dioxide—NaOH extraction procedure was repeated three more times and the resulting toluene solution concentrated under vacuum to give (S)-1-benzyl-3-(p-toluenesulfonylamino)pyrrolidine, 4, as an amber oil. The oil was dissolved in warm (60°–70° C.) toluene (15 mL) and a solution (30 mL) of isopropyl alcohol saturated with hydrogen chloride gas was added. The solution was stirred and cooled to −5° C. where it was maintained for 3 hours. The solid product was collected and washed with isopropyl alcohol and ether and vacuum dried to give (S)-1-benzyl-3-(p-toluenesulfonylamino)pyrrolidine hydrochloride as an off-white solid (46.5 g, 74% combined yield for Steps 3 and 4). A portion was recrystallized from isopropyl alcohol: mp 179°-181° C.

STEP 5: (S)-3-Amino-1-benzylpyrrolidine, 5

(S)-1-Benzyl-3-(p-toluenesulfonylamino)pyrrolidine hydrochloride (40.0 g), phenol (12.0 g) and 30% hydrogen bromide in acetic acid (200 mL) were combined and heated in a sealed flask at 105° C. to 125° C. for a period of 55 minutes. The resulting red solution was concentrated under vacuum to remove excess acetic acid and hydrogen bromide and the thick oil dissolved in water (500 mL) and toluene (150 mL). The layers were separated and the aqueous layer extracted with toluene (50 mL) and diethyl ether (30 mL) and treated with 28% ammonium hydroxide (11 mL) to give a pH of 8.5. This solution was extracted with toluene (25 mL) and all of the organic extracts discarded. The remaining aqueous layer was treated with 50% NaOH (145 mL) and extracted with toluene (3×50 mL). The combined toluene extracts were concentrated to an oil (19.2 g) which was distilled under vacuum (bp 104°-106° C. at 2.5 mm Hg) to give (S)-3-amino-1-benzylpyrrolidine, 5, (18.2 g, 94%) as a colorless oil: $[\alpha]_{25} = +11.2°$.

EXAMPLE 2

STEP 6:
1-Benzyl-3-(S)-[2-(S)-(tert-butoxycarbonylamino)propionylamino]-pyrrolidine N-(tert-Butoxycarbonyl)-L-alanine (12.8 g) was dissolved in methylene chloride (50 mL) and the solution cooled to −5° C., and treated with N-methylmorpholine (6.7 g). The resulting mixture was stirred and cooled to −5° to −10° C. and a cold (−5° C.) solution of isobutyl chloroformate (8.5 g) in methylene chloride (100 mL) added slowly while keeping the temperature at or below −5° C. The mixture was stirred for another 30 minutes at −5° to −10° C. To this mixture was then added a cold (0° C.) solution of (S)-3-amino-1-benzylpyrrolidine (10.0 g) in methylene chloride (100 mL) while keeping the temperature between 0° and −10° C. The reaction mixture was stirred at 0° to −5° C. for 1 hour and then at 15° to 25° C. for 2 hours. The mixture was treated with 300 mL of demineralized water and the layers separated. The organic phase was extracted with a solution of sodium bicarbonate (18.5 g) in demineralized water (200 mL) followed by demineralized water (300 mL). The organic phase was dried over sodium sulfate (50 g) and the product solution concentrated under vacuum to give 1-benzyl-3-(S)-[2-(S)-(tert-butoxycarbonylamino)propionylamino]pyrrolidine (21.3 g) as an off-white solid (mp: 102°-105° C.) which was used in the next step without further purification.

STEP 7:
3-(S)-[2-(S)-(tert-Butoxycarbonylamino)propionylamino]pyrrolidine

1 Benzyl-3-(S)-[2-(S)-(tert-butoxycarbonylamino)propionylamino]pyrrolidine (21.3 g) was dissolved in methanol (250 mL), and hydrogenated over 20% palladium hydroxide on charcoal, 50% water wet (5.0 g) at 50 psig and 25° to 40° C. until the uptake of hydrogen ceased. The reaction was then filtered through celite to remove the catalyst and the residue rinsed with methanol (100 mL) and the combined filtrates concentrated under vacuum to give 3-(S)-[2-(S)-(tert-butoxycarbonylamino)propionylamino]pyrrolidine (14.6 g) as a colorless oil which crystallized on standing: HPLC: 99% S,S isomer. A portion was recrystallized from methyl tert-butyl ether: mp 137°-138° C.

EXAMPLE 3

(S)-2-(p-Toluenesulfonylamino)-1,4-butanediol, 2

Dimethyl N-(p-toluenesulfonyl)-L-aspartate, (2 0 g; J. M. Theobald, M. W. Williams, G. T. Young, *J. Chem. Soc.,* 1927 (1963)) was dissolved in tetrahydrofuran (20 mL) and NaBH₄ (1.5 g) and LiCl (1.5 g) added and the mixture stirred at 0° C. for 60 to 64 hours. Ten percent hydrochloric acid (10 mL) was slowly added (caution! gas evolution) and the mixture extracted with ethyl acetate (3×20 mL). The combined organic extracts were concentrated and the residue dried under vacuum to give (S)-2-(p-toluene-sulfonylamino)-1,4-butanediol, 2, as an off-white solid (1.95 g; HPLC: 97.7%).

We claim:

1. A compound of the formula

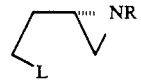

wherein L is halo or alkyl- or arylsulfonyloxy and R is an alkyl or arylsulfonyl group.

2. A compound of claim 1 and being (S)-2-(2'-methanesulfonyloxyethyl)-1-(p-toluenesulfonyl)aziridine.

3. 1-Benzyl-3-(S)-[2-(S)-(tert-butoxycarbonylamino)-propionylamino]-pyrrolidine.

* * * * *